United States Patent [19]

Lunn

[11] 4,061,861
[45] Dec. 6, 1977

[54] 7-[α-(2,3-DIHYDRO-2-OXO-1H-BENZIMIDAZOL-1-YLCARBONYL-AMINO)ARYLACETAMIDO]CEPHALOSPORINS

[75] Inventor: William H. W. Lunn, Indianapolis, Ind.

[73] Assignee: Eli Lilly and Company, Indianapolis, Ind.

[21] Appl. No.: 698,431

[22] Filed: June 21, 1976

[51] Int. Cl.$^2$ .............................. C07D 501/34
[52] U.S. Cl. ................... 544/30; 424/246; 544/26; 544/27
[58] Field of Search ....................... 260/243 C

[56] References Cited

U.S. PATENT DOCUMENTS 3,966,709  6/1976  Konig et al. ............. 260/243 C

FOREIGN PATENT DOCUMENTS 7,407,815  6/1974  Netherlands ............. 260/243 C

OTHER PUBLICATIONS

70–02178, 1/24/70, Japan Fuji. Ltd., 260/243c 6 pp. (Abstract 121564g C.A., vol. 72, 1970).

Primary Examiner—Nicholas S. Rizzo
Assistant Examiner—D. B. Springer
Attorney, Agent, or Firm—William C. Martens, Jr.; Everet F. Smith

[57] ABSTRACT

Cephalosporin antibiotics of the formula

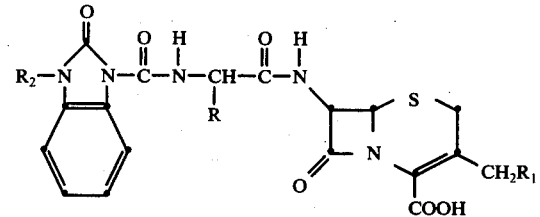

in which, for example, R is phenyl, hydroxyphenyl, halophenyl, thienyl, or furyl; $R_1$ is hydrogen, carbamoyloxy, acetoxy, a lower alkyl substituted 1H-tetrazol-5-ylthio or 1,3,4-thiadiazol-5-ylthio group; and $R_2$ is hydrogen or methyl; are highly active broad spectrum antibiotics especially useful in the treatment of infections attributable to the gram-negative microorganisms.

9 Claims, No Drawings

7-[α-(2,3-DIHYDRO-2-OXO-1H-BENZIMIDAZOL-1-YLCARBONYL-AMINO)ARYLACETAMIDO]-CEPHALOSPORINS

BACKGROUND OF THE INVENTION

Cephalosporin compounds having a substituted amino group in the α-position of the 7-acylamino side chain have been described in the literature. In U.S. Pat. Nos. 3,673,183 and 3,708,479, α-ureido cephalosporanic acids are disclosed. Penicillins and cephalosporins having an α-(3-imidoylureido)arylacetamido side chain are described in U.S. Pat. Nos. 3,634,405 and 3,646,024, respectively. In U.S. Pat. No. 3,687,949, cephalosporins having an α-(3-acylureido)arylacetamido side chain are disclosed. This latter patent defines a wide variety of acyl groups attached to the terminal nitrogen of the α-ureido group of the 7-arylacetamido side chain. Also, in U.S. Pat. No. 3,579,514, cephalosporins having an α-(3-guanyl-1-ureido)arylacetamido side chain are described.

A new class of cephalosporin compounds having a substituted carbamido substituent in the α-position of the 7-arylacetamido side chain has now been discovered. This class of compounds represents the basis of this invention. These compounds, active against both gram-negative and gram-positive pathogens and particularly against Pseudomonas microorganisms, are prepared by acylating the free amino group in the 7-position side chain of a cephalosporin including, for example, cephaloglycin, 7-(D-α-amino-α-phenylacetamido)-3-(1-lower alkyl-1H-tetrazol-5-ylthiomethyl)-3-cephem-4-carboxylic acid, 7-(D-α-amino-α-phenylacetamido)-3-(5-lower alkyl-1,3,4-thiadiazol-2-ylthiomethyl)-3-cephem-4-carboxylic acid, and the like, as well as hydroxy and halogen derivatives thereof with an appropriately structured acylating agent.

SUMMARY OF THE INVENTION

Thus, this invention is directed to a compound of the formula

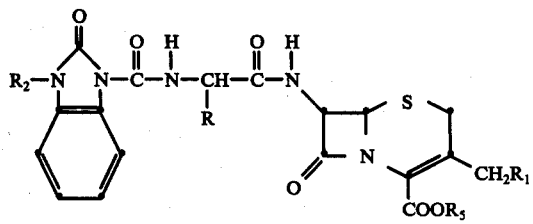

in which R is phenyl, monohydroxyphenyl, dihydroxyphenyl, monohalophenyl, monohydroxy substituted monohalophenyl, thienyl, or furyl;

$R_1$ is hydrogen, acetoxy,

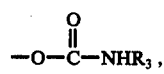

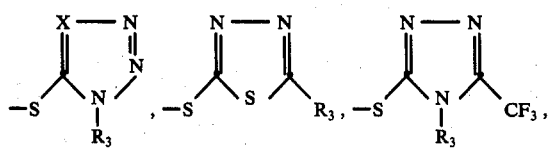

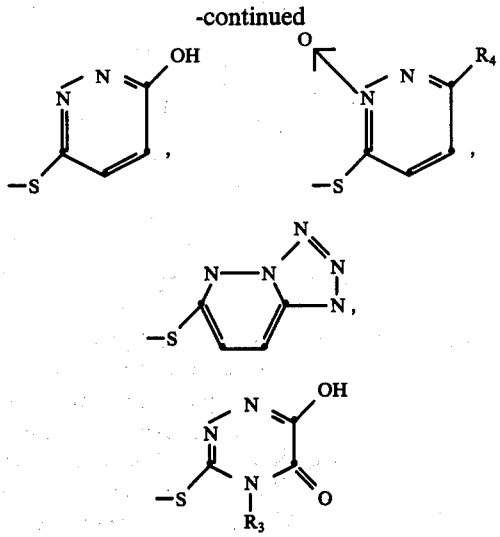

in which, in any of the above, X is =CH— or =N—, $R_3$ is hydrogen or $C_1-C_4$ alkyl, and $R_4$ is methyl, methoxy, or chloro;

$R_2$ is hydrogen or methyl; and $R_5$ is hydrogen, indanyl, phthalidyl, an acyloxymethyl group of the formula

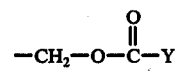

in which Y is $C_1-C_4$ alkyl or phenyl, or, when $R_5$ is hydrogen, the pharmaceutically acceptable non-toxic salts thereof.

The new cephalosporins described and claimed herein are active against a broad spectrum of microorganisms, and, accordingly, are useful for combating infections in warm-blooded animals. Administration generally is by the parenteral route.

Furthermore, the cephalosporins described herein include biologically active esters, for example, the acetoxymethyl or the benzoyloxymethyl esters, and also include pharmaceutically useful salts, particularly the alkali metal salts, such as the lithium, sodium, and potassium salts.

DETAILED DESCRIPTION OF THE INVENTION

As indicated above, this invention relates to new cephalosporin antibiotic compounds having the following general formula I

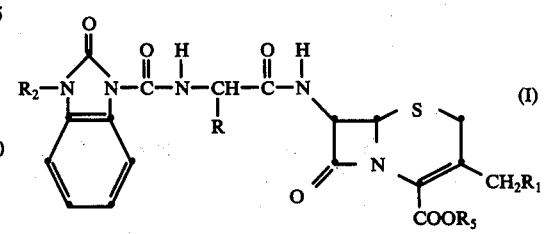

in which R, $R_1$, $R_2$, and $R_5$ are as aforedescribed.

$R_2$ above is defined as hydrogen or methyl. In the foregoing definition, the substituted α-amino moiety has the formula

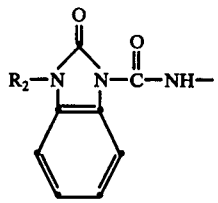

This moiety thus includes 2,3-dihydro-2-oxo-1H-benzimidazol-1-ylcarbonylamino-, and 3-methyl-2,3-dihydro-2-oxo-1H-benzimidazol-1-ylcarbonylamino-.

The group R of the compounds of this invention is phenyl, monohydroxyphenyl, dihydroxyphenyl, monohalophenyl, monohydroxy substituted monohalophenyl, thienyl, or furyl. The term "halo" as used herein refers to fluoro, chloro, and bromo, and, preferably, to chloro. Representative examples of the group R are phenyl, 3-hydroxyphenyl, 4-hydroxyphenyl, 3,5-dihydroxyphenyl, 4-chlorophenyl, 4-bromophenyl, 3-fluorophenyl, 2-chlorophenyl, 2-hydroxyphenyl, 3-chloro-4-hydroxyphenyl, 3-hydroxy-4-bromophenyl, 3-fluoro-4-hydroxyphenyl, 2-thienyl, 3thienyl, 2-furyl, 3-furyl, and the like. Preferably, R is phenyl, p-hydroxyphenyl, or 2-thienyl, and, most preferably, R is p-hydroxyphenyl.

The novel cephalosporin compounds represented by the general formula I have in the 3-position a substituent of the formula —CH$_2$R$_1$ in which R$_1$ is hydrogen, acetoxy, N-alkyl substituted and unsubstituted carbamoyloxy, or any of a group of specific heterocyclylthio substituents.

The following therefore are illustrative of a portion of the group —CH$_2$R$_1$ in formula I above: methyl, acetoxymethyl, carbamoyloxymethyl, N-methylcarbamoyloxymethyl, N-ethylcarbamoyloxymethyl, N-n-propylcarbamoyloxymethyl, N-isopropylcarbamoyloxymethyl, N-n-butylcarbamoyloxymethyl, N-isobutylcarbamoyloxymethyl, and the like.

In addition, the 3-substituent of the cephalosporins of this invention is selected from a group of specifically structured heterocyclylthiomethyl moieties.

Included among these are 1H-unsubstituted and substituted tetrazol-5-ylthiomethyl groups of the formula

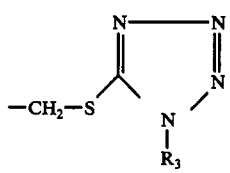

Specifically, these include tetrazol-5-ylthiomethyl, 1-methyltetrazol-5-ylthiomethyl, 1-ethyltetrazol-5-ylthiomethyl, 1-n-propyltetrazol-5-ylthiomethyl, 1-isopropyltetrazol-5-ylthiomethyl, 1-n-butyltetrazol-5-ylthiomethyl, 1-isobutyltetrazol-5-ylthiomethyl, and the like.

Another class of these substituents includes 1-unsubstituted and substituted 1,2,3-triazol-5-ylthiomethyl groups of the formula

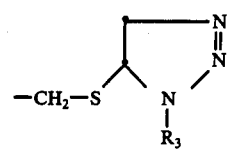

Illustrative of this class are 1,2,3-triazol-5-ylthiomethyl, 1-methyl-1,2,3,-triazol-5-ylthiomethyl, 1-ethyl-1,2,3-triazol-5-ylthiomethyl, 1-n-propyl-1,2,3-triazol-5-ylthiomethyl, 1-isopropyl-1,2,3-triazol-5-ylthiomethyl, 1-n-butyl-1,2,3-triazol-5-ylthiomethyl, 1-isobutyl-1,2,3-triazol-5-ylthiomethyl, and the like.

Another class of these substituents includes 1-unsubstituted and substituted 5-trifluoromethyl-1,3,4-triazol-2-ylthiomethyl groups of the formula

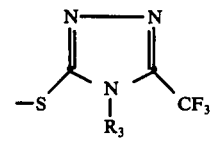

Illustrative groups of this class are 5-trifluoromethyl-1,3,4-triazol-2-ylthiomethyl, 1-methyl-5-trifluoromethyl-1,3,4-triazol-2-ylthiomethyl, 1-ethyl-5-trifluoromethyl-1,3,4-triazol-2-ylthiomethyl, 1-n-propyl-5-trifluoromethyl-1,3,4-triazol-2-ylthiomethyl, 1-isopropyl-5-trifluoromethyl-1,3,4-triazol-2-ylthiomethyl, 1-n-butyl-5-trifluoromethyl-1,3,4-triazol-2-ylthiomethyl, 1-t-butyl-5-trifluoromethyl-1,3,4-triazol-2-ylthiomethyl, and the like. Substituents of this kind are disclosed in U.S. Pat. No. 3,796,801.

Another class of these substituents includes 5-unsubstituted or substituted 1,3,4-thiadiazol-2-ylthiomethyl groups of the formula

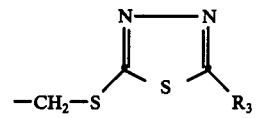

Illustrative groups of this class are 1,3,4-thiadiazol-2-ylthiomethyl, 5-methyl-1,3,4-thiadiazol-2-ylthiomethyl, 5-ethyl-1,3,4-thiadiazol-2-ylthiomethyl, 5-n-propyl-1,3,4-thiadiazol-2-ylthiomethyl, 5-isopropyl-1,3,4-thiadiazol-2-ylthiomethyl, 5-isobutyl-1,3,4-thiadiazol-2-ylthiomethyl, 5-sec-butyl-1,3,4-thiadiazol-2-ylthiomethyl, and the like.

Another such group is 3-hydroxypyridazin-6-ylthiomethyl, which has the formula

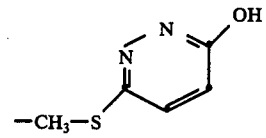

This particular substituent is disclosed in U.S. Pat. No. 3,813,376.

A further substituent is a 1-oxide-3-substitutedpyridazin-6-ylthiomethyl having the formula

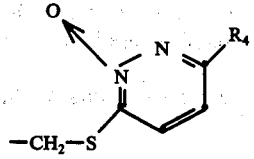

These particular substituents are disclosed in U.S. Pat. No. 3,892,737, and include 1-oxide-3-methylpyridazin-6-ylthiomethyl, 1-oxide-3-methoxypyridazin-6-ylthiomethyl, and 1-oxide-3-chloropyridazin-6-ylthiomethyl.

Another such group is tetrazolo [4,5-b]pyridazin-6-ylthiomethyl having the formula

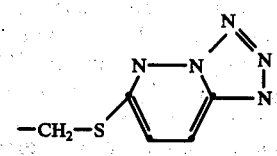

This substituent is disclosed in U.S. Pat. No. 3,814,755.

A final substituent is a 5-oxo-6-hydroxy-4,5-dihydro-1,2,4-triazin-3-ylthiomethyl having the formula

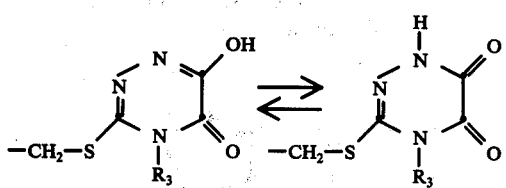

These substituents are described in Belgian Pat. No. 831,787. As noted, this structure also can be represented by the tautomeric diketo form. The 3-mercapto-1,2,4-triazines which represent the source of these substituents are prepared by a method described in Pesson et al., Bulletin de la Societe Chemique de France, (1970), pages 1590–1599. They are illustrated by the following groups: 5-oxo-6-hydroxy-4,5-dihydro-1,2,4-triazin-3-ylthiomethyl; 4-methyl-5-oxo-6-hydroxy-4,5-dihydro-1,2,4-triazin-3-ylthiomethyl; 4-ethyl-5-oxo-6-hydroxy-4,5-dihydro-1,2,4-triazin-3-ylthiomethyl; 4-n-propyl-5-oxo-6-hydroxy-4,5-dihydro-1,2,4-triazin-3-ylthiomethyl; 4-isopropyl-5-oxo-6-hydroxy-4,5-dihydro-1,2,4-triazin-3-ylthiomethyl; 4-n-butyl-5-oxo-6-hydroxy-4,5-dihydro-1,2,4-triazin-3-ylthiomethyl; 4-sec-butyl-5-oxo-6-hydroxy-4,5-dihydro-1,2,4-triazin-3-ylthiomethyl; 4-isobutyl-5-oxo-6-hydroxy-4,5-dihydro-1,2,4-triazin-3-ylthiomethyl; and the like.

Preferably, the 3-substituent is acetoxy or

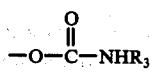

(carbamoyloxy). Of the carbamoyloxy groups, $R_3$ preferably is hydrogen.

Other preferred 3-substituents are selected from the group consisting of 1H-unsubstituted and substituted tetrazol-5-ylthiomethyl; 1-unsubstituted and substituted 1,2,3-triazol-5-ylthiomethyl; 5-unsubstituted and substituted 1,3,4-thiadiazol-2-ylthiomethyl; and 4-unsubstituted and substituted 5-oxo-6-hydroxy-4,5-dihydro-1,2,4-triazin-3-ylthiomethyl. Of the above, the group $R_3$ preferably is hydrogen or methyl, and, most preferably, is methyl.

The compounds of this invention are prepared by acylation of the appropriate 7-(D-α-amino-α-arylacetamido)-3-cephem-4-carboxylic acid. This cephalosporin has the structure

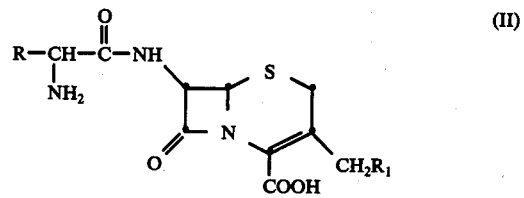

in which R and $R_1$ are as aforedescribed.

The reagent used to achieve acylation of the above cephalosporin and thus preparation of the compounds of this invention is the acyl chloride of 2-oxobenzimidazolecarboxylic acid or 3-methyl-2-oxobenzimidazole-1-carboxylic acid. Preparation of the acylating agent is accomplished by treating 2-oxobenzimidazole or 3-methyl-2-oxobenzimidazole in a suitable solvent with phosgene.

2-Oxobenzimidazole is prepared by treating o-phenylenediamine with urea at a temperature of about 150°–200° C. The corresponding 3-methyl-2-oxobenzimidazole is prepared analogously from N-methyl-o-phenylenediamine, the latter being available by methylating o-phenylenediamine using methyl iodide at a temperature of about 65° C. to about 90° C.

As indicated hereinabove, the compounds of this invention are prepared by reacting a compound of formula II with the appropriate acylating agent. The starting materials represented by formula II are available from a 7-amino cephalosporin of the formula

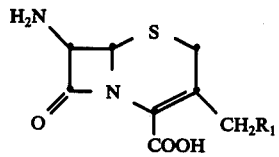

In general, the 7-amino compound can be reacted with the anhydride formed from an α-(t-butyloxycarbamido)arylacetic acid of the formula

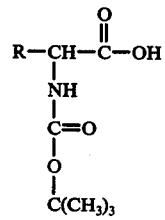

and isobutyl chloroformate. Following the acylation, the t-butyloxycarbonyl protecting group is removed by known methods, for example, by treatment with trifluoroacetic acid in the cold, or, alternatively, by treatment with p-toluenesulfonic acid in acetonitrile.

The product, a compound of formula II, then is reacted with the hereinbefore described acylating agent to effect acylation of the free α-amino group in the 7-position side chain. This acylation is carried out in an inert solvent and at a temperature generally from about −5° C. to about 30° C. Solvents such as acetonitrile, tetrahydrofuran, N,N-dimethylformamide, and N,N-dimethylacetamide can be used in the acylation reaction. Preferred solvents are tetrahydrofuran or acetonitrile. The acylation is greatly promoted by first treating the cephalosporin starting material with a silylating agent such as N,O-bis-(trimethylsilyl)acetamide (BSA), N-trimethylsilylacetamide (MSA), and the like. The silylating agent provides protection for the free carboxyl of the cephalosporin starting material and also facilitates ready acylation of the free amino group. Furthermore, the cephalosporin, in the form of its trimethylsilyl ester, will be solubilized prior to reaction with the acylating agent. This will also greatly assist in effecting formation of the desired product.

A hydrogen halide acceptor also can be included in the acylation reaction mixture. The hydrogen halide acceptor is non-alkaline, becoming activated only upon generation of the hydrogen chloride produced as by-product of the acylation. Typical hydrogen halide acceptors include alkylene oxides such as propylene oxide, butylene oxide, and the like. A preferred hydrogen halide acceptor is propylene oxide.

By the above methods, the free acid cephalosporins of this invention, that is, those in which R₅ is hydrogen, are prepared.

The compounds of this invention, in their free acid form (R₅ = H), form pharmaceutically acceptable salts with inorganic bases such as the alkali metal carbonates and bicarbonates. For example, the lithium, sodium, and potassium salts can be formed from lithium, sodium, and potassium carbonate, respectively, by conventional procedures.

The cephalosporin antibiotics of this invention in the form of their free acid or their alkali metal salts can be converted to their corresponding biologically active esters. These are compounds in which R₅ is indanyl, phthalidyl, or

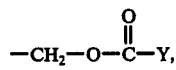

in which Y is C₁-C₄ alkyl or phenyl.

The biologically active esters in which R₅ is

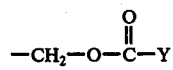

are prepared by reacting an alkali metal salt of the free acid cephalosporin, for example, the lithium, sodium, or potassium salt, with an acyloxymethyl halide of the formula

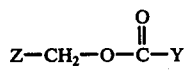

in which Z is chloro or bromo and Y is C₁-C₄ alkyl or phenyl. Acyloxymethyl halides which can be employed include chloromethyl acetate, bromomethyl acetate, bromomethyl propionate, chloromethyl pivaloate, chloromethyl benzoate, and the like.

Preparation of the acyloxymethyl esters is carried out by reacting the alkali metal salt form of the cephalosporin acid in an inert solvent with at least a molar equivalent of the bromomethyl or the chloromethyl ester, for example, bromomethyl acetate, at room temperature or at a slightly elevated temperature up to about 40°-45° C. A solvent such as acetone, tetrahydrofuran, dioxane, N,N-dimethylformamide, methylene chloride, and the like, can be used.

The indanyl ester compounds of this invention are those in which R₅ is

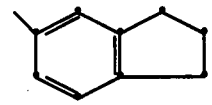

These are prepared by reacting 5-indanol in an inert solvent such as dioxane or tetrahydrofuran with the free acid form of a cephalosporin of this invention in the presence of a condensing agent such as a diimide, for example, N,N'-dicyclohexylcarbodiimide. The reaction is carried out with stirring at about 20°-35° C. for about six to about eight hours. The indanyl ester is isolated by diluting the reaction mixture with water and then filtering it to remove the insoluble dicyclohexylurea. The ester then is extracted from the filtrate.

Alternatively, the indanyl ester can be prepared by reacting the mixed acid anhydride formed from the free acid cephalosporin and acetic acid with 5-indanol.

Phthalidyl ester compounds of this invention are those in which the group R₅ is

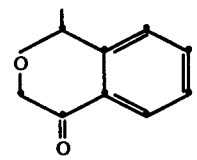

These are obtained by reacting bromophthalide having the formula

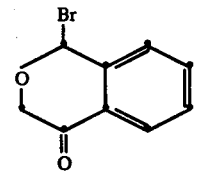

with a salt of the free acid cephalosporin. This esterification can be carried out in N,N-dimethylformamide, N,N-dimethylacetamide, dioxane, tetrahydrofuran, or mixtures thereof, by slowly warming a mixture of equimolar amounts of the cephalosporin salt, for example, the sodium or the potassium salt, and bromophthalide.

Illustrative of the compounds of this invention are the following:

7-[α-(2,3-dihydro-2-oxo-1H-benzimidazol-1-ylcarbonylamino)phenylacetamido]-3-methyl-3-cephem-4-carboxylic acid;

7-[α-(2,3-dihydro-2-oxo-1H-benzimidazol-1-ylcarbonylamino)phenylacetamido]-3-acetoxymethyl-3-cephem-4-carboxylic acid;

7-[α-(2,3-dihydro-2-oxo-1H-benzimidazol-1-ylcarbonylamino)phenylacetamido]-3-carbamoyloxymethyl-3-cephem-4-carboxylic acid;

7-[α-(2,3-dihydro-2-oxo-1H-benzimidazol-1-ylcarbonylamino)phenylacetamido]-3-(N-methylcarbamoyloxymethyl)-3-cephem-4-carboxylic acid;

7-[α-(2,3-dihydro-2-oxo-1H-benzimidazol-1-ylcarbonylamino)phenylacetamido]-3-(tetrazol-5-ylthiomethyl)-3-cephem-4-carboxylic acid;

7-[α-(2,3-dihydro-2-oxo-1H-benzimidazol-1-ylcarbonylamino)phenylacetamido]-3-(1-methyltetrazol-5-ylthiomethyl)-3-cephem-4carboxylic acid;

7-[α-(2,3-dihydro-2-oxo-1H-benzimidazol-1-ylcarbonylamino)phenylacetamido]-3-(1-ethyltetrazol-5-ylthiomethyl)-3-cephem-4-carboxylic acid;

7-[α-(2,3-dihydro-2-oxo-1H-benzimidazol-1-ylcarbonylamino)phenylacetamido]-3-(1-isopropyltetrazol-5-ylthiomethyl)-3-cephem-4-carboxylic acid;

7-[α-(2,3-dihydro-2-oxo-1H-benzimidazol-1-ylcarbonylamino)phenylacetamido)]-3-(1,2,3-triazol-5-ylthiomethyl)-3-cephem-4-carboxylic acid;

7-[α-(2,3-dihydro-2-oxo-1H-benzimidazol-1-ylcarbonylamino)phenylacetamido]-3-(1-methyl-1,2,3-triazol-5-ylthiomethyl)-3-cephem-4-carboxylic acid;

7-[α-(2,3-dihydro-2-oxo-1H-benzimidazol-1-ylcarbonylamino)phenylacetamido]-3-(1-ethyl-1,2,3-triazol-5-ylthiomethyl)-3-cephem-4-carboxylic acid;

7-[α-(2,3-dihydro-2-oxo-1H-benzimidazol-1-ylcarbonylamino)phenylacetamido]-3-(1-n-butyl-1,2,3-triazol-5-ylthiomethyl)-3-cephem-4-carboxylic acid;

7-[α-(2,3-dihydro-2-oxo-1H-benzimidazol-1-ylcarbonylamino)plenylacetamido]-3-trifluoromethyl-1,3,4-triazol-5-ylthiomethyl)-3-cephem-4-carboxylic acid;

7-[α-(2,3-dihydro-2-oxo-1H-benzimidazol-1-ylcarbonylamino)phenylacetamido]-3-(1-methyl-5-trifluoromethyl-1,3,4-triazol-5-ylthiomethyl)-3-cephem-4-carboxylic acid;

7-[α-(2,3-dihydro-2-oxo-1H-benzimidazol-1-ylcarbonylamino)phenylacetamido]-3-(1-ethyl-5-trifluoromethyl-1,3,4-triazol-5-ylthiomethyl)-3-cephem-4-carboxylic acid;

7-[-(2,3-dihydro-2-oxo-1H-benzimidazol-1-ylcarbonylamino)phenylacetamido]-3-(1-n-butyl-5-trifluoromethyl-1,3,4-triazol-5-ylthiomethyl)-3-cephem-4-carboxylic acid;

7-[α-(2,3-dihydro-2-oxo-1H-benzimidazol-1-ylcarbonylamino)phenylacetamido]-3-(1,3,4-thiadiazol-2-ylthiomethyl)-3-cephem-4-carboxylic acid;

7-[α-(2,3-dihydro-2-oxo-1H-benzimidazol-1-ylcarbonylamino)phenylacetamido]-3-(5-methyl-1,3,4-thiadiazol-2-ylthiomethyl)-3-cephem-4-carboxylic acid;

7-[α-(2,3-dihydro-2-oxo-1H-benzimidazol-1-ylcarbonylamino)phenylacetamido]-3-(5-ethyl-1,3,4-thiadiazol-2-ylthiomethyl)-3-cephem-4-carboxylic acid;

7-[α-(2,3-dihydro-2-oxo-1H-benzimidazol-1-ylcarbonylamino)phenylacetamido]-3-(5-n-propyl-1,3,4-thiadiazol-2-ylthiomethyl)-3-cephem-4-carboxylic acid;

7-[α-(2,3-dihydro-2-oxo-1H-benzimidazol-1-ylcarbonylamino)phenylacetamido]-3-(3hydroxypyridazin-6-ylthiomethyl)-3-cephem-4-carboxylic acid;

7-[α-(2,3-dihydro-2-oxo-1H-benzimidazol-1-ylcarbonylamino)phenylacetamido]-3-(1-oxide-3-methylpyridazin-6-ylthiomethyl)-3-cephem-4-carboxylic acid;

7-[α-(2,3-dihydro-2-oxo-1H-benzimidazol-1ylcarbonylamino)phenylacetamido]-3-(1-oxide-3-methoxypyridazin-6-ylthiomethyl)-3-cephem-4-carboxylic acid;

7-[α-(2,3-dihydro-2-oxo-1H-benzimidazol-1ylcarbonylamino)phenylacetamido]-3-(1-oxide-3-chloropyridazin-6-ylthiomethyl)-3-cephem-4-carboxylic acid;

7-[α-(2,3-dihydro-2-oxo-1H-benzimidazol-1 ylcarbonylamino)phenylacetamido]-3-(tetrazolo-[4,5-b]-pyridazin-6-ylthiomethyl)-3-cephem-4-carboxylic acid;

7-[α-(2,3-dihydro-2-oxo-1H-benzimidazol-1-ylcarbonylamino)phenylacetamido]-3-(5-oxo-6-hydroxy-4,5-dihydro-1,2,4-triazin-3-ylthiomethyl)-3-cephem-4-carboxylic acid;

7-[α-(2,3-dihydro-2-oxo-1H-benzimidazol-1-ylcarbonylamino)phenylacetamido]-3-(4-methyl-5-oxo-6-hydroxy-4,5-dihydro-1,2,4-triazin-3-ylthiomethyl)-3-cephem-4-carboxylic acid;

7-[α-(2,3-dihydro-2-oxo-1H-benzimidazol-1-ylcarbonylamino)phenylacetamido]-3-(4-ethyl-5-oxo-6-hydroxy-4,5-dihydro-1,2,4-triazin-3-ylthiomethyl)-3-cephem-4-carboxylic acid;

7-[α-(2,3-dihydro-2-oxo-1H-benzimidazol-1-ylcarbonylamino)phenylacetamido]-3-(4-isobutyl-5-oxo-6-hydroxy-4,5-dihydro-1,2,4-triazin-3-ylthiomethyl)-3-cephem-4-carboxylic acid;

7-[α-(2,3-dihydro-2-oxo-1H-benzimidazol-1-ylcarbonylamino)-4-hydroxyphenylacetamido]-3-carbamoyloxymethyl-3-cephem-4-carboxylic acid;

7-[α-(2,3-dihydro-2-oxo-1H-benzimidazol-1-ylcarbonylamino)-4-hydroxyphenylacetamido]-3-(1-methyl-1,2,3-triazol-5-ylthiomethyl)-3-cephem-4-carboxylic acid;

7-[α-(2,3-dihydro-2-oxo-1H-benzimidazol-1-ylcarbonylamino)-4-hydroxyphenylacetamido]-3-(1-methyltetrazol-5-ylthiomethyl)-3-cephem-4-carboxylic acid;

7-[α-(2,3-dihydro-2-oxo-1H-benzimidazol-1-ylcarbonylamino)-4-hydroxyphenylacetamido]-3-(5-methyl-1,3,4-thiadiazol-2-ylthiomethyl)-3-cephem-4-carboxylic acid;

7-[α-(2,3-dihydro-2-oxo-1H-benzimidazol-1-ylcarbonylamino)-4-hydroxyphenylacetamido]-3-(4-methyl-5-oxo-6-hydroxy-4,5-dihydro-1,2,4-triazin-3-ylthiomethyl)-3-cephem-4-carboxylic acid;

7-[α-(3-methyl-2,3-dihydro-2-oxo-1H-benzimidazol-1-ylcarbonylamino)phenylacetamido]-3-acetoxymethyl-3-cephem-4-carboxylic acid;

7-[α-(3-methyl-2,3-dihydro-2-oxo-1H-benzimidazol-1-ylcarbonylamino)phenylacetamido]-3-(5-methyl-1,3,4-thiadiazol-2-ylthiomethyl)-3-cephem-4-carboxylic acid;

7-[α-(3-methyl-2,3-dihydro-2-oxo-1H-benzimidazol-1-ylcarbonylamino)phenylacetamido]-3-methyl-3-cephem-4-carboxylic acid;

7-[α-(3-methyl-2,3-dihydro-2-oxo-1H-benzimidazol-1-ylcarbonylamino)phenylacetamido]-3-carbamoyloxymethyl-3-cephem-4-carboxylic acid;

7-[α-(3-methyl-2,3-dihydro-2-oxo-1H-benzimidazol-1-ylcarbonylamino)phenylacetamido]-3-(N-ethylcarbamoyloxymethyl)-3-cephem-4-carboxylic acid;

7-[α-(2,3-dihydro-2-oxo-1H-benzimidazol-1-ylcarbonylamino)-3-hydroxyphenylacetamido]-3-(1-methyltetrazol-5-ylthiomethyl)-3-cephem-4-carboxylic acid;

7-[α-(2,3-dihydro-2-oxo-1H-benzimidazol-1-ylcarbonylamino)-3-chlorophenylacetamido]-3-(4-methyl-5-oxo-6-hydroxy-4,5-dihydro-1,2,4-triazin-3-ylthiomethyl)-3-cephem-4-carboxylic acid;

7-[α-(2,3-dihydro-2-oxo-1H-benzimidazol-1-ylcarbonylamino)-2,4-dihydroxyphenylacetamido]-3-(1,3,4-thiadiazol-2-ylthiomethyl)-3-cephem-4-carboxylic acid;

7-[α-(2,3-dihydro-2-oxo-1H-benzimidazol-1-ylcarbonylamino)-3-chloro-4-hydroxyphenylacetamido]-3-(1-methyl-1,2,3-triazol-5-ylthiomethyl)-3-cephem-4-carboxylic acid;

7-[α-(2,3-dihydro-2-oxo-1H-benzimidazol-1-ylcarbonylamino)-2-thienylacetamido]-3-(5-methyl-1,3,4-thiadiazol-2-ylthiomethyl)-3-cephem-4-carboxylic acid;

7-[α-(2,3-dihydro-2-oxo-1H-benzimidazol-1-ylcarbonylamino)-3-thienylacetamido]-3-(1-methyltetrazol-5-ylthiomethyl)-3-cephem-4-carboxylic acid;

against the indicated microorganisms. The MIC values were obtained using the gradient plate in vitro method for determining antibiotic activity.

TABLE
ANTIBIOTIC ACTIVITY OF 2,3-DIHYDRO-2-OXO-1H-BENZIMIDAZOL-1-YLCARBONYLAMINO SUBSTITUTED CHEPHALOSPORINS

| Test Organism[1] | Minimum Inhibitory Concentration (mcg.ml.) Test Compound[2] | | | | |
|---|---|---|---|---|---|
| | A | B | C | D | E |
| Shigella sp. | 100 | 16 | 55 | 15 | 120 |
| Escherichia coli | 140 | 9 | 72.5 | 14 | 160 |
| Klebsiella pneumoniae | 90 | 7 | 25 | 19 | 100 |
| Aerobacter aerogenes | 140 | 21.8 | 120 | 30 | >200 |
| Salmonella heidelberg | 120 | 15.0 | 80 | 18 | 120 |
| Pseudomonas aeruginosa | 16 | 12.0 | 8.5 | 8 | 10.0 |
| Serratia marcescens | >200 | 120 | >200 | >200 | >200 |
| V41 | 8.0 | 1.0 | 5.0 | 3.0 | 5.0 |
| V32 | 11.0 | 6.0 | 6.0 | 3.0 | 5.0 |
| X400 | >20 | >20 | >20 | 16 | 180 |
| V84 | 8.0 | 0.9 | 0.9 | 0.6 | 0.7 |

[1]Test organisms V41, V32, and V84 are penicillin resistant Staphylococcus. X-400 is a methicillin resistant Staphylococcus.
[2]Test compounds:
A. 7-[α-(2,3-dihydro-2-oxo-1H-benzimidazol-1-ylcarbonylamino)phenylacetamido]-3-acetoxy-methyl-3-cephem-4-carboxylic acid.
B. 7-α-(2,3-dihydro-2-oxo-1H-benzimidazol-1-ylcarbonylamino)phenylacetamido]-3-(1-methyltetrazol-5-ylthiomethyl)-3-cephem-4-carboxylic acid.
C. 7-[α-(3-methyl-2,3-dihydro-2-oxo-1H-benzimidazol-1-ylcarbonylamino)phenylacetamido]-3-acetoxy-methyl-3-cephem-4-carboxylic acid.
D. 7-[α-(3-methyl-2,3-dihydro-2-oxo-1H-benzimidazol-1-ylcarbonylamino)phenylacetamido]-3-(1-methyltetrazol-5-ylthiomethyl)-3-cephem-4-carboxylic acid.
E. 7-[α-(2,3-dihydro-2-oxo-1H-benzimidazol-1-ylcarbonylamino)-4-hydroxyphenylacetamido]-3-carbamoyloxymethyl-3-cephem-4-carboxylic acid.

7-[α-(2,3-dihydro-2-oxo-1H-benzimidazol-1-ylcarbonylamino)-2-furylacetamido]-3-carbamoyloxymethyl-3-cephem-4-carboxylic acid;

7-[α-(2,3-dihydro-2-oxo-1H-benzimidazol-1-ylcarbonylamino)-3-furylacetamido]-3-acetoxymethyl-3-cephem-4-carboxylic acid;

7-[α-(3-methyl-2,3-dihydro-2-oxo-1H-benzimidazol-1-ylcarbonylamino)-2-thienylacetamido]-3-(1-methyltetrazol-5-ylthiomethyl)-3-cephem-4-carboxylic acid;

7-[α-(3-methyl-2,3-dihydro-2-oxo-1H-benzimidazol-1-ylcarbonylamino)-4-hydroxyphenylacetamido]-3-(4-ethyl-5-oxo-6-hydroxy-4,5-dihydro-1,2,4-triazin-3-ylthiomethyl)-3-cephem-4-carboxylic acid;

7-[α-(3-methyl-2,3-dihydro-2-oxo-1H-benzimidazol-1-ylcarbonylamino)-3,5-dihydroxyphenylacetamido]-3-(1-ethyltetrazol-5-ylthiomethyl)-3-cephem-4-carboxylic acid;

7-[α-(3-methyl-2,3-dihydro-2-oxo-1H-benzimidazol-1-ylcarbonylamino)-3-hydroxy-4-fluoro-phenylacetamido]-3-methyl-3-cephem-4-carboxylic acid;

7-[α-(3-methyl-2,3-dihydro-2-oxo-1H-benzimidazol-1-ylcarbonylamino)-2-fluorophenylacetamido]-3-(1-n-butyl-1,2,3-triazol-5-ylthiomethyl)-3-cephem-4-carboxylic acid; and the like.

The above compounds are in the form of their free acids. It is evident that these compounds are described for the purpose of illustration only and, moreover, that these compounds can be in the form of their pharmaceutically acceptable salts or their biologically active esters.

The cephalosporin antibiotics of this invention are effective in inhibiting the growth of a wide spectrum of pathogenic microorganisms of both the gram-positive and the gram-negative type. In particular, they are effective against Pseudomonas microorganisms.

The antibiotic activity of the cephalosporin compounds of this invention is illustrated by the data provided in the following Table of representative compounds. The values in the Table are the minimum inhibitory concentrations (MIC) for the test compounds The cephalosporin antibiotics of this invention in which $R_5$ is hydrogen as well as the pharmaceutically acceptable salts thereof are useful in combatting infections in warm-blooded mammals when administered parenterally in non-toxic doses of from about 10 to about 500 mg./kg. body weight. The ester compounds of this invention are useful antibiotics when administered orally in non-toxic doses of from about 50 to about 750 mg./kg. body weight.

The following are provided as specific illustrations of the preparation of acylating agents which are employed in preparing the compounds of this invention. A — Preparation of 2,3-Dihydro-2-oxo-1H-benzimidazol-1-ylcarbonyl chloride.

To a slurry of 8.0 grams of 2-oxobenzimidazole in 400 ml. of o-dichlorobenzene cooled in a dry ice-acetone bath were added 60 ml. of phosgene. The entire mixture was transferred to a pressurized vessel and was heated with agitation at 80° C. for eight hours and then at room temperature for seven hours. The mixture was cooled in a dry ice-acetone bath and was vented carefully to allow escape of any hydrogen chloride gas. The mixture was transferred to a two liter round bottom flask, dry benzene being employed to facilitate complete transfer. The phosgene and benzene were removed in vacuo, and the resulting slurry was cooled in a dry ice-acetone bath, filtered, and the collected solid was washed with hexane and dried in vacuo to give 8.6 grams of the title compound as a light brown solid, melting point 179°-184° C. (dec.). B — Preparation of 3-Methyl-2,3-dihydro-2-oxo-1H-benzimidazol-1- ylcarbonyl chloride.

To one liter of methanol were added 89 grams (0.82 mole) of o-phenylenediamine and 25.7 ml. (0.41 mole) of methyl iodide. The mixture was refluxed for 2 hours, and an additional 25.7 ml. (0.41 mole) of methyl iodide then were added. The total mixture was refluxed for 12 hours. The major portion of the methanol then was removed in vacuo. The residual brown oil was poured into two liters of crushed ice, and the pH of the mixture was raised to 9.0 by addition of potassium hydroxide.

The resulting mixture then was extracted with ethyl ether, and the extract was dried over potassium carbonate. The ether was removed in vacuo, and the residue was distilled at about 120° C./8 mm. to obtain N-methyl-o-phenylenediamine as a yellow oil which turned brown upon standing.

A mixture of 24.4 grams (0.2 mole) of N-methyl-o-phenylenediamine and 14.4 grams (0.24 mole) of urea was prepared. The mixture was stirred for 16 hours in an oil bath maintained at 175° C. The reaction mixture then was cooled to about 80° C., 250 ml. of alcohol were added, and the mixture was refluxed for 20 minutes and then was filtered while hot. The filtrate was allowed to cool to room temperature and was refrigerated overnight. The crystals that formed were filtered, dried, and recrystallized from water to obtain 7.84 grams of 3-methyl-2-oxobenzimidazole, melting point 188°–189° C.

To 40 ml. of dried benzene were added 1 gram of N-methyl-2-oxobenzimidazole and 10 ml. of phosgene. The mixture was heated at 80° C. for eight hours and then was evaporated to dryness to afford 1.2 grams of the title compound as a light yellow foam.

The following examples are provided for the purpose of illustrating the preparation of the compounds of this invention. They are not intended to be limiting up the scope of the invention.

EXAMPLE 1

Preparation of 7-[α-(2,3-Dihydro-2-oxo-1H-benzimidazol-1-ylcarbonylamino)phenylacetamido]-3-acetoxymethyl-3-cephem-4-carboxylic acid.

To 15 ml. of dry acetonitrile were added 883 mg. (2 mmoles) of 7-(α-aminophenylacetamido)-3-acetoxymethyl-3-cephem-4-carboxylic acid dihydrate. The mixture was cooled, and 3.13 grams (14.4 mmoles) of N,O-bis-trimethylsilylacetamide were added. Solution was complete within two minutes. The resulting mixture then was stirred at room temperature, and 452 mg. (2.3 mmoles) of 2,3-dihydro-2-oxo-1H-benzimidazol-1-ylcarbonyl chloride were added, the temperature of the mixture rising from 25° C. to 28° C. Analysis of a sample of the reaction mixture after 30 minutes by thin-layer chromatography (TLC) indicated that reaction was complete. After two hours, the reaction mixture was slowly dropped into rapidly stirred ice water, the pH of the resulting suspension being 1.9. The pH was adjusted to 1.7 by addition of hydrochloric acid. The mixture was filtered, and the solid which was collected was washed with dilute hydrochloric acid and air-dried to give 1.16 grams of the title compound as a buff-colored powder.

NMR (DMSOd$_6$) 11.90 (broad s, 1H, benzimidazole N-H); 9.85 and 9.62 (two broad d, each 1H, CONH); 7.96 (m, 1H, benzimidazole 7-H); 7.45 (broad, 5H, phenyl H); 7.17 (broad, 3H, benzimidazole 4-, 5-, and 6-H); 5.8 (broad m, 2H, benzyl-H and 7α-H); 5.07 (d, 1H, 6α-H); 4.84 (q, 2H, 3'—CH$_2$); and 3.50 (broad, 2H, 2—CH$_2$) ppm from tetramethylsilane.

EXAMPLE 2

Preparation of 7-[α-(2,3-Dihydro-2-oxo-1H-benzimidazol-1-ylcarbonylamino)phenylacetamido]-3-(1-methyltetrazol-5-ylthiomethyl)-3-cephem-4-carboxylic acid.

To 15 ml. of dry acetonitrile were added 923 mg. (2 mmoles of 7-(α-aminophenylacetamido)-3-(1-methyltetrazol-5-ylthiomethyl)-3-cephem-4-carboxylic acid and 1.62 grams (8 mmoles) of N,O-bis-trimethylsilylacetamide. Solution was complete within 5 minutes. To the mixture then were added 452 mg. (2.3 mmoles) of 2,3-dihydro-2-oxo-1H-benzimidazol-1-ylcarbonyl chloride. The temperature of the mixture rose about 4°, and solution was complete within 5 minutes. After 20 minutes, a sample of the reaction mixture, analyzed by TLC, indicated that the reaction was complete. After two hours, the mixture (containing some solid) was slowly dropped into rapidly stirred ice water. A gummy solid deposited and was changed to particulate solid upon further stirring of the mixture. The suspension (pH 1.9) was adjusted to pH 1.7 by addition of concentrated hydrochloric acid. The mixture was filtered, and the solid was washed with dilute hydrochloric acid and air-dried to give 1.16 grams of the title compound as a buff-colored powder.

NMR (DMSOd$_6$) 11.90 (broad s, 1H, benzimidazole N-H); 9.85 and 9.62 (two broad d, each 1H, CONH); 7.94 (m, 1H, benzimidazole 7-H); 7.43 (broad, 5H, phenyl-H); 7.17 (broad, 3H, benzimidazole 4-, 5-, and 6-H); 5.8 (broad m, 2H, benzyl-H and 7α-H); 5.03 (d, 1H, 6α-H); 4.29 (broad, 2H, 3'—CH$_2$, visible in D$_2$O exchange but obscured in DMSOd$_6$ alone); 3.94 (s, 3H, N—CH$_3$); and 3.63 (broad, 2H, 2—CH$_2$) ppm from tetramethylsilane.

EXAMPLE 3

Preparation of 7-[α-(3-Methyl-2,3-dihydro-2-oxo-1H-benzimidazol-1-ylcarbonylamino)phenylacetamido]-3-acetoxymethyl-3-cephem-4-carboxylic acid.

To 30 ml. of dry tetrahydrofuran (THF) were added 441 mg. (1 mmole) of 7-(α-aminophenylacetamido)-3-acetoxymethyl-3-cephem-4-carboxylic acid dihydrate and 0.97 ml. (4 mmoles) of N,O-bis-trimethylsilylacetamide. The mixture was stirred until solution was complete, and then a solution of 210 mg. (1 mmole) of 3-methyl-2,3-dihydro-2-oxo-1H-benzimidazol-1-ylcarbonyl chloride in 5 ml. of THF was added at room temperature. The reaction mixture was stirred for 50 minutes. Methanol (5 ml.) was added to the mixture; however, no precipitation occurred. The mixture then was evaporated to a volume of about 10 ml., and the resulting precipitate was filtered. A mixture of 50 ml. of ethyl acetate and 50 ml. of water was added to the filtrate, and the pH of the mixture was adjusted to 7.5 by addition of sodium bicarbonate. The layers were separated, and the aqueous layer was acidified to pH 2.0 by addition of 1N hydrochloric acid. The acidic mixture then was extracted twice with 50 ml. of a 6:1 mixture of ethyl acetate and tetrahydrofuran. The organic extract was dried over magnesium sulfate, filtered, and evaporated slowly to a volume of about 10 ml. The concentrate was cooled overnight, and the resulting crystalline precipitate was filtered and dried to obtain 275 mg. of the title compound.

NMR (DMSOd$_6$) 9.92 and 9.70 (two broad d, each 1H, CONH); 7.95 (m, 1H, benzimidazole-7H); 7.47 (broad, 5H, phenyl-H); 7.20 (broad, 3H, benzimidazole 4-, 5-, and 6-H); 5.8 (broad, 2H, benzyl-H and 7α-H); 5.04 (d, 1H, 6α-H); 4.83 (q, 2H, 3'—CH$_2$); 3.46 (broad, 2H, 2—CH$_2$); 3.37 (s, 3H, NCH$_3$); and 2.02 (s, 3H, OCOCH$_3$) ppm from tetramethylsilane.

EXAMPLE 4

Preparation of 7-[α-(3-Methyl-2,3-dihydro-2-oxo-1H-benzimidazol-1-ylcarbonylamino)phenylacetamido]-3-(1-methyltetrazol-5-ylthiomethyl)-3-cephem-4-carboxylic acid.

Employing the method of Example 3, 461 mg. (1 mmole) of 7-(α-aminophenylacetamido)-3-(1-methyltetrazol-5-ylthiomethyl)-3-cephem-4-carboxylic acid were reacted with 210 mg. of 3-methyl-2,3-dihydro-2-oxo-1H-benzimidazol-1-ylcarbonyl chloride to obtain 410 mg. of the title compound as a light yellow powder.

NMR (DMSOd$_6$) 9.92 and 9.69 (two broad d, each 1H, CONH); 7.95 (broad, 1H, benzimidazole-7-H); 7.48 (broad, 5H, phenyl-H); 7.21 (broad s, 3H, benzimidazole 4,5 and 6-H); 5.8 (broad m, 2H, benzyl-H and 7α-H); 5.02 (d, 1H, 6α-H); 4.28 (broad, 2H, 3'—CH$_2$); 3.94 (s, 3H, tetrazole NCH$_3$); 3.60 (broad, 2H, 2—CH$_2$); and 3.37 (s, 3H, benzimidazole N—CH$_3$) ppm from tetramethylsilane.

EXAMPLE 5

Preparation of 7-[α-(2,3-dihydro-2-oxo-1H-benzimidazol-1-ylcarbonylamino)-4-hydroxyphenylacetamido]-3-carbamoyloxymethyl-3-cephem-4-carboxylic acid.

To 8 ml. of dry acetonitrile were added 422 mg. (1 mmole) of 7-(α-amino-4-hydroxyphenylacetamido)-3-carbamoyloxymethyl-3-cephem-4-carboxylic acid. The mixture was stirred in a bath comprising acetone and wet ice, and 1.62 grams (8 mmoles) of N,O-bis-trimethylsilylacetamide were added. Solution was complete within about 5 minutes. The mixture was stirred for an additional 5 minutes, and 0.7 ml. of propylene oxide was added followed, after an additional 5 minutes, by 197 mg. (1 mmole) of 2,3-dihydro-2-oxo-1H-benzimidazol-1-ylcarbonyl chloride. The mixture was stirred for 105 minutes and then was rotary evaporated to about one-half volume. The concentrated reaction mixture was slowly added to rapidly-stirred ice water, and the pH of the resulting mixture, containing a percipitated gum, was adjusted from 3.8 to 1.6. The resulting mixture then was sonicated, with hardening of the gum. The resulting hard lumps were broken, sonicated, filtered, washed with dilute hydrochloric acid (pH 1.8), and air-dried to give 251 mg. of a buff powder. The filtrate was concentrated to remove acetonitrile and was filtered to afford an additional 20 mg. of a buff-colored powder. The solids were combined and added to 40 ml. of methylene chloride. The mixture was sonicated and filtered to recover 210 mg. of solid. The solid was added to 100 ml. of methylene chloride, sonicated, and filtered to obtain 200 mg. of the title compound.

NMR (DMSOd$_6$) 11.74 (broad s, 1H, benzimidazole N-H); 9.61 and 9.38 (two broad d, each 1H, CONH); 7.95 (m, 1H, benzimidazole 7-H); 7.4–7.0 (complex, 6H, two p-hydroxyphenyl ring-H, benzimidazole 4-, 5-, and 6H, and one carbamate-H); 6.76 (d, 2H, p-hydroxyphenyl ring-H); 6.58 (broad, 1H, carbamate-H); 5.7 (broad m, 2H, benzyl-H and 7α-H); 5.07 (d, 1H, 6α-H); 4.73 (broad q, 2H, 3'—CH$_2$); and 3.45 (broad, 2H, 2—CH$_2$) ppm from tetramethylsilane.

I claim:
1. A compound of the formula

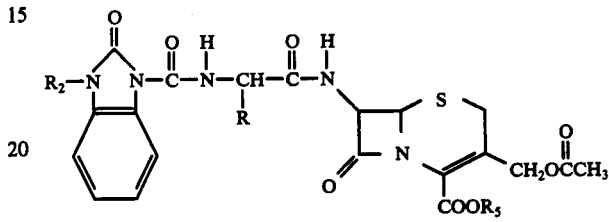

in which R is phenyl, monohydroxyphenyl, dihydroxyphenyl, monohalophenyl, monohydroxy substituted monohalophenyl, thienyl, or furyl;

R$_2$ is hydrogen or methyl; and R$_5$ is hydrogen, indanyl, phthalidyl, an acyloxymethyl group of the formula

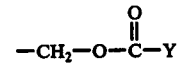

in which Y is C$_1$–C$_4$ alkyl or phenyl, or, when R$_5$ is hydrogen, the pharmaceutically acceptable non-toxic salts thereof.

2. Compound of claim 1, in which R$_2$ is hydrogen.
3. Compound of claim 1, in which R$_2$ is methyl.
4. Compound of claim 1, in which R is phenyl.
5. Compound of claim 4, in which R$_2$ is hydrogen.
6. Compound of claim 4, in which R$_2$ is methyl.
7. Compound of claim 1, in which R is p-hydroxyphenyl.
8. Compound of claim 7, in which R$_2$ is hydrogen.
9. Compound of claim 7, in which R$_2$ is methyl.

* * * * *